United States Patent [19]
Koenig et al.

[11] 3,991,093

[45] Nov. 9, 1976

[54] SUBSTITUTED m-TRIFLUOROMETHYLPHENYLUREA DERIVATIVES

[75] Inventors: Karl-Heinz Koenig, Frankenthal; Rudolph Kolbinger, Speyer; Adolph Fischer, Mitterstadt, all of Germany

[73] Assignee: BASF Aktiengesellschaft, Ludwigshafen (Rhine), Germany

[22] Filed: June 3, 1974

[21] Appl. No.: 476,149

Related U.S. Application Data

[62] Division of Ser. No. 215,664, Jan. 5, 1972, Pat. No. 3,847,971.

[30] Foreign Application Priority Data

Jan. 15, 1971 Germany............................ 2101698

[52] U.S. Cl................................ 260/453 R; 71/98; 71/120; 260/544 C; 260/553 A
[51] Int. Cl.$^2$................ C07C 127/19; C07C 83/08; A01N 9/12; A01N 9/20
[58] Field of Search..................... 260/553 A, 453 R

[56] References Cited

UNITED STATES PATENTS

| | | | |
|---|---|---|---|
| 2,708,677 | 5/1955 | Suter et al. | 260/553 A X |
| 3,072,719 | 1/1963 | Beaver et al. | 260/553 A |
| 3,520,925 | 7/1970 | Koenig et al. | 260/553 A |
| 3,558,303 | 1/1971 | Gobeil | 71/120 |
| 3,673,248 | 6/1972 | Petersen | 260/553 A X |

FOREIGN PATENTS OR APPLICATIONS

| | | | |
|---|---|---|---|
| 699,773 | 12/1964 | Canada | 260/553 A |
| 1,142,354 | 2/1969 | United Kingdom | 260/553 A |

*Primary Examiner*—Floyd D. Higel
*Assistant Examiner*—Thomas A. Waltz
*Attorney, Agent, or Firm*—Johnston, Keil, Thompson & Shurtleff

[57] ABSTRACT

New and valuable substituted m-trifluoromethylphenylurea derivatives having a good herbicidal action; herbicides containing these compounds as active ingredients; and a process for controlling the growth of unwanted plants with these compounds.

1 Claim, No Drawings

SUBSTITUTED M-TRIFLUOROMETHYLPHENYLUREA DERIVATIVES

This is a division of application Ser. No. 215,664, filed Jan. 5, 1972, now U.S. Pat. No. 3,847,971.

The present invention relates to new and valuable substituted m-trifluoromethylphenylurea derivatives having a good herbicidal action and the use of these compounds as herbicides.

It is known to use m-trifluoromethylphenylurea derivatives, e.g. N-m-trifluoromethylphenyl-N′,N′-dimethylurea, as herbicides. However, their action is not satisfactory.

We have now found that substituted m-trifluoromethylphenylurea derivatives of the formula

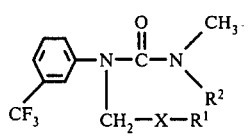

where $R^1$ denotes alkyl, alkenyl, alkynyl, cycloalkyl, aralkyl, or aryl, X denotes oxygen or sulfur, and $R^2$ denotes alkyl of 1 to 3 carbon atoms, methoxy or hydrogen, have excellent herbicidal properties.

The herbicidal action is particularly in evidence on grassy weeds, millet types and dicotyledonous weeds at application rates of 1 to 5 kg per hectare. The compounds are suitable for controlling unwanted plants in the following crops: cotton, Indian corn, cereals and sugar cane. The active ingredients, which may be in a finely distributed state, e.g., in the form of a solution, dispersion, emulsion or dust, may be applied by treating the unwanted plants directly, or the soil in which the growth of unwanted plants is to be prevented.

The ureas may be synthesized by reacting the N-m-trifluoromethylphenyl-N-α-methylether (or thioether)-carbamoyl chlorides with the appropriate primary or secondary amines.

The starting material for the substituted carbamyl chloride is N-m-trifluoromethylphenyl-N-chloromethylcarbamyl chloride. The latter is produced in two stages. In the first stage m-trifluoromethylaniline is reacted with paraformaldehyde, and in the second the hexahydrotriazine or N-methylene-(m-trifluoromethylaniline) formed is phosgenated. The N-m-trifluoromethylphenyl-N-α-methylether (or thioether)-carbamyl chlorides are obtained by reacting N-m-trifluoromethylphenyl-N-chloromethylcarbamyl chlorides with the appropriate alcohols or mercaptans.

EXAMPLE 1

Preparation of N-m-trifluoromethylphenyl-N-methoxymethyl-N′N,-N′-dimethylurea 322 parts (by weight) of m-trifluoromethylaniline and 120 parts of paraformaldehyde are boiled under reflux in 200 parts of benzene. The water which forms is removed. When the reaction is over and no more water is formed, the reaction mixture is distilled in a water jet vacuum up to a bottoms temperature of 100° C. In this manner the 1,3,5-tri-(m-trifluoromethylphenyl)-hexahydrotriazine is obtained.

At 0° C, 2 moles of phosgene in 50 parts of chloroform is placed in a vessel and, at 0° C, a solution of 1 mole of 1,3,5-tri(m-trifluoromethylphenyl)-hexahydrotriazine and 50 parts of chloroform is added. The reaction product is allowed to heat up slowly to room temperature and it is then boiled under reflux for 2 to 3 hours. The solvent is distilled off and the residue fractionated. The yield is 45%; boiling point (0.5 mm) 110° C. In this manner N-m-trifluoromethylphenyl-N-chloromethylcarbamyl chloride is obtained.

1 mole of N-m-trifluoromethylphenyl-N-chloromethylcarbamyl chloride and 6 moles of methanol are stirred for 5 hours at 50° C, while passing through nitrogen. The mixture is stirred overnight, nitrogen still being passed in. Subsequently, excess methanol is distilled off and the residue fractionated. The yield is at least 90%, the boiling point (0.3 mm Hg) 98° C. In this manner N-m-trifluoromethylphenyl-N-methoxymethylcarbamoyl chloride is obtained.

The following carbamyl chlorides may be prepared analogously.

TABLE 1

| X | $R^1$ | molecular formula | molecular weight | b.p. or m.p. [° C] |
|---|---|---|---|---|
| O | —CH(CH₃)₂ | $C_{12}H_9ClF_3NO_2$ | 295.5 | 0.5 mm Hg 122–124 |
| O | —CH₂—C≡CH | $C_{12}H_{13}ClF_3NO_2$ | 291.5 | 0.3 mm Hg 116–118 |
| O | —CH₂—CH(CH₂)₃CH₃, C₂H₅ | $C_{17}H_{23}ClF_3NO_2$ | 365.5 | 0.3 mm Hg 148–150 |
| O | —(CH₂)₁₁—CH₃ | $C_{21}H_{31}ClF_3NO_2$ | 421.5 | 0.4 mm Hg 154–156 |
| O | —⟨H⟩ | $C_{15}H_{17}ClF_3NO_2$ | 335.5 | 0.5 mm Hg 139–142 |

TABLE 1-continued

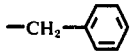

| X | R¹ | molecular formula | molecular weight | b.p. or m.p. [° C] |
|---|---|---|---|---|
| O | —CH₂—C₆H₅ | $C_{16}H_{13}ClF_3NO_2$ | 343.5 | 0.3 mm Hg 144–145 |
| O | —CH₂CH₂—C₆H₅ | $C_{17}H_{15}ClF_3NO_2$ | 357.5 | 0.3 mm Hg 152–153 |
| O | —C₆H₅ | $C_{15}H_{11}ClF_3NO_2$ | 329.5 | 0.1 mm Hg 143 |
| S | —CH₃ | $C_{10}H_9ClF_3NOS$ | 283.5 | 0.4 mm Hg 108–110 |
| S | —(CH₂)₁₁CH₃ | $C_{21}H_{31}ClF_3NOS$ | 437.5 | 0.5 mm Hg 160–161 |

0.21 mole of dimethylamine is dissolved in 100 ml of cyclohexane; at room temperature 0.1 mole of N-m-trifluoromethylphenyl-N-methoxymethylcarbamyl chloride is dripped in, the whole is stirred overnight, and water is subsequently added. The organic phase is separated, the solvent is distilled off and the residue fractionally distilled in vacuo. There is thus obtained N-m-trifluoromethylphenyl-N-methoxymethyl-N',N'-dimethylurea; boiling point (0.01 mm Hg): 87° to 90° C.

The following urea derivatives may be prepared analogously:

EXAMPLE 2

0.1 mole of O,N-dimethylhydroxylamine hydrochloride is dissolved in 30 ml of water. 70 ml of chloroform is then added. At 10° C, a solution of 0.1 mole of NaOH in 16 ml of water is dripped in and subsequently, also at 10° C, 0.1 mole of N-m-trifluoromethylphenyl-N-methoxymethylcarbamyl chloride. After stirring for 2 hours, the chloroform layer is separated, the solvent is distilled off and the residue is fractionally distilled. There is thus obtained N-m-trifluoromethylphenyl-N-methoxymethyl-N'-methyl-N'-methoxyurea; boiling point (0.05 mm Hg): 91° to 94° C.

TABLE 2

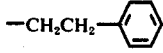

| X | R¹ | R² | molecular formula | molecular weight | b.p. or m.p. [° C] |
|---|---|---|---|---|---|
| O | CH₃ | CH₃ | $C_{12}H_{15}F_3N_2OS$ | 292 | 0.01 mm Hg 92–93 |
| S | CH₃ | OCH₃ | $C_{12}H_{15}F_3N_2O_2S$ | 308 | 0.03 mm Hg 91–92 |
| O | —CH₂—C≡CH | CH₃ | $C_{14}H_{15}F_3N_2O_2$ | 300 | 0.01 mm Hg 84 |
| O | cyclohexyl | CH₃ | $C_{17}H_{23}F_3N_2O_2$ | 344 | 0.02 mm Hg 108–110 |
| O | —CH₃ | H | $C_{11}H_{13}F_3N_2O_2$ | 262 | 0.01 mm Hg 111–113 |
| O | —CH₂—C₆H₅ | H | $C_{17}H_{17}F_3N_2O_2$ | 338 | 0.05 mm Hg 112–114 |
| O | —CH₂—C₆H₅ | CH₃ | $C_{18}H_{19}F_3N_2O_2$ | 352 | 0.02 mm Hg 102–103 |
| O | —(CH₂)₁₁CH₃ | CH₃ | $C_{23}H_{37}F_3N_2O_2$ | 430 | 0.01 mm Hg 124–127 |
| O | —CH(CH₃)₂ | CH₃ | $C_{14}H_{19}F_3N_2O_2$ | 304 | 0.01 mm Hg 99–101 |
| O | —C₂H₅ | CH₃ | $C_{13}H_{17}F_3N_2O_2$ | 290 | 0.02 mm Hg 89–92 |

We have found that, surprisingly, the strong herbicidal action is not essentially dependent on the type of the substituent $R^1$.

The herbicides according to the invention may be used as solutions, emulsions, suspensions or dusts. The form of application depends entirely on the purpose for which the agents are being used; in any case it should ensure a fine distribution of the active ingredient.

For the preparation of solutions to be sprayed directly, hydrocarbons having boiling points higher than 150° C, e.g. tetrahydronaphathalene or alkylated naphthalenes, or organic liquids having boiling points higher than 150° C and having one or more than one functional group, e.g. the keto group, the ether group, the ester group or the amide group, this group or these groups being attached as substituent(s) to a hydrocarbon chain or being a component of a heterocyclic ring, may be used as spray liquids.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g. polyethylene oxide adducts. Concentrates which are suitable for dilution with water may be prepared from active ingredient, emulsifying or dispersing agent and possibly solvent. Oils may also be used to produce an oil dispersion.

Dusts may be prepared by mixing or grinding the active ingredients with a solid carrier, e.g. kieselguhr, talc, clay or fertilizers.

The following examples demonstrate the use of the new active ingredients.

EXAMPLE 3

In a greenhouse, loamy sandy soil was filled into pots and sown with the seeds of Gossypium hirsutum, Echinochloa crus-galli, Poa annua, Poa trivialis and Chenopodium album.

The soil was then treated with 2 kg per hectare of each of the following active ingredients, each being dispersed in 500 liters of water per hectare:

I
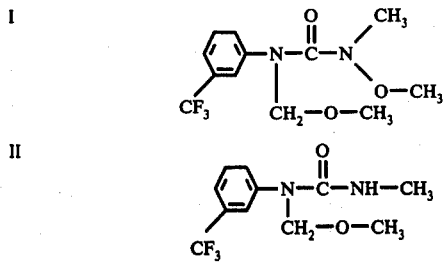

II and, for comparison,

III N-m-trifluoromethylphenyl-N′,N′-dimethylurea.

After 4 to 5 weeks it was ascertained that active ingredients I and II had a stronger herbicidal action than III.

The results of this experiment are given in the following table:

| | Active ingredient | | |
|---|---|---|---|
| Crop plants: | I | II | III |
| Gossypium hirsutum | 0 | 0 | 0 |
| Unwanted plants: | | | |
| Echinochloa crus-galli | 86 | 87 | 80 |
| Poa annua | 95 | 92 | 85 |
| Poa trivialis | 90 | 90 | 80 |
| Chenopodium album | 97 | 97 | 95 |

0 = no damage
100 = complete destruction

EXAMPLE 4

The plants Triticum vulgare, Echinochloa crus-galli, Poa annua, Poa trivialis, Chenopodium album and Sinapis arvensis were treated at a growth height of 6 to 18 cm with 1.5 kg per hectare of each of I, II and III, each active ingredient being dispersed in 500 liters of water per hectare. After 3 to 4 weeks it was ascertained that I and II had a stronger herbicidal action than III on the broadleaved and grassy weeds.

The results of this experiment are given in the following table:

| | Active ingredient | | |
|---|---|---|---|
| | I | II | III |
| Crop plant: | | | |
| Triticum vulgare | 5 | 0 | 5 |
| Unwanted plants: | | | |
| Echinochloa crus-galli | 92 | 94 | 85 |
| Poa annua | 90 | 92 | 82 |
| Poa trivialis | 93 | 91 | 80 |
| Chenopodium album | 98 | 97 | 95 |
| Sinapis arvensis | 99 | 98 | 95 |

0 = no damage
100 = complete destruction

EXAMPLE 5

Waste land with Raphanus raphanistrum, Vicia villosa, Convolvulus arvensis, Geleopsis tetrahit, Cyperus esculentus, Echinochloa crus-galli, Digitaria sanguinalis, Cynodon dactylon, Lolium perenne, Alopecurus myosuroides and Agropyron repens growing on it was treated at a growth height of the plants of 10 to 30 cm with 4 kg per hectare of each of I and II, each active ingredient being dispersed in 500 liters of water per hectare. After 3 weeks the broadleaved and grassy weeds were completely withered.

EXAMPLE 6

Plots were sown with Chenopodium album, Sinapis arvensis, Cyperus esculentus, Echinochloa crus-galli, Lolium multiflorum, Dactylis glomerata and Setaria viridis. Subsequently the plots were treated with 4 kg per hectare of each of I and II, each active ingredient being dispersed in 500 liters of water per hectare. After 5 weeks it was ascertained that the plants were completely withered.

EXAMPLE 7

90 parts by weight of compound I is mixed with 10 parts by weight of N-methyl--pyrrolidone. A mixture is obtained which is suitable for application in the form of very fine drops.

EXAMPLE 8

20 parts by weight of compound II is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound I is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

3 parts by weight of compound II is intimately mixed with 97 parts by weight of particulate kaolin. A dust is obtained containing 3% by weight of the active ingredient.

EXAMPLE 11

30 parts by weight of compound I is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:

1. A substituted m-trifluoromethylphenylurea derivative of the formula

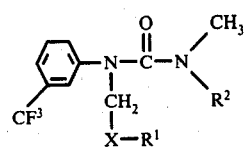

where $R^1$ denotes methyl; X denotes oxygen; and $R^2$ denotes methoxy.

* * * * *